United States Patent
Igarashi et al.

(10) Patent No.: US 6,524,530 B1
(45) Date of Patent: Feb. 25, 2003

(54) SAMPLE COLLECTING MEMBER AND WIPING INSPECTION INSTRUMENT

(75) Inventors: Toshinori Igarashi, Noda (JP); Noriaki Hattori, Noda (JP); Seiji Murakami, Noda (JP); Tatsuya Sakakibara, Noda (JP); Morisaku Saito, Tokyo (JP)

(73) Assignee: Kikkoman Corporation, Chiba-ken (JP)

( * ) Notice: Subject to any disclaimer, the term of this patent is extended or adjusted under 35 U.S.C. 154(b) by 0 days.

(21) Appl. No.: 09/529,375

(22) PCT Filed: Oct. 12, 1998

(86) PCT No.: PCT/JP98/04586

§ 371 (c)(1), (2), (4) Date: Apr. 12, 2000

(87) PCT Pub. No.: WO99/19709

PCT Pub. Date: Apr. 22, 1999

(30) Foreign Application Priority Data

| Oct. 13, 1997 | (JP) | 9-293225 |
| Feb. 13, 1998 | (JP) | 10-046396 |
| Aug. 31, 1998 | (JP) | 10-244684 |
| Sep. 29, 1998 | (JP) | 10-274715 |

(51) Int. Cl.[7] .................................................. G01N 33/48
(52) U.S. Cl. ........................ 422/58; 422/58; 422/61; 422/102; 436/165; 436/174; 435/304.2
(58) Field of Search ............................ 422/58, 61, 102, 422/100; 436/165–166, 169, 174, 177–178; 435/287.1, 304.2, 309.1

(56) References Cited

U.S. PATENT DOCUMENTS

| 4,353,868 A | 10/1982 | Joslin et al. |
| 4,707,450 A | * 11/1987 | Nason ........................ 206/438 |
| 4,770,853 A | * 9/1988 | Bernstein ...................... 422/102 |
| 5,096,062 A | 3/1992 | Burkardt et al. |

FOREIGN PATENT DOCUMENTS

| EP | PCT/US96/00524 | 1/1996 |
| EP | PCT/GB96/03166 | 12/1996 |
| JP | 58-169553 | 5/1982 |
| JP | 6-201701 | 12/1992 |
| JP | 7-34370 | 7/1993 |
| JP | 8-54390 | 8/1994 |
| JP | 8-292189 | 4/1995 |

* cited by examiner

*Primary Examiner*—Lyle A. Alexander
(74) *Attorney, Agent, or Firm*—Merchant & Gould P.C.

(57) ABSTRACT

A wipe inspecting instrument comprising a sample collecting member and a reactive reagent container. The sample collecting member comprises a tubular main body having both upper and lower ends thereof opened, a sample wiping member removably fitted to the upper open portion of the main body and an extracting liquid container disposed below the main body. The sample wiping member includes a retaining member inserted into the upper part of the main body and a cotton swab held by the retaining member. Further, the sample collecting member includes a splash-proofing member disposed at a lower part of the extracting liquid container, for preventing the splash of the extracting liquid. The reactive reagent container has a test tube shape and so inserted into the open portion at the lower end of the main body as to be capable of moving up and down.

17 Claims, 20 Drawing Sheets

SAMPLE COLLECTING MEMBER AND WIPING INSPECTION INSTRUMENT

TECHNICAL FIELD

The present invention relates to an instrument for collecting bacteria in a liquid or on the surface of a solid body and measuring the quantity of the collected bacteria through a light-emitting reaction and the like.

BACKGROUND ART

Test instruments for wiping bacteria from the surface of a solid body by the use of a cotton swab and measuring the quantity of the collected bacteria are conventionally known as disclosed in U.S. Pat. No. 4,353,868 "SPECIMEN COLLECTING DEVICE", WO9703209 "TEST APPARATUS SYSTEM AND METHOD FOR THE DETECTION OF TEST SAMPLES", and WO9723596 "SAMPLING AND ASSAY DEVICE".

U.S. Pat. No. 4,353,868 is directed to an inspection instrument which comprises a tubular body having a convex portion at a lower part thereof, a cotton swab inserted into the main body, and an absorbent material attached to a top end of the main body. In use, after wiping, a reactive reagent container is pushed up to break a seal material. Then, the main body is put upside down to place a cotton-capped tip of the swab in contact with the reagent by means of the absorbent material.

WO9703209 discloses a test instrument which comprises a tubular main body, a cotton swab fitted therein, and a reagent container fitted into a top end of the main body. For detecting the quantity of bacteria, the swab is pressed down to break a seal material of the reagent container to thereby put a swab tip into contact with the reagent.

WO9723596 is directed to an arrangement wherein members and parts are unitarily joined. It was achieved by adding a member for rupturing seal material, to the instrument of WO9703209.

The instrument of U.S. Pat. No. 4,353,868 is slow in reaction because the swab tip is contacted with the reagent via the absorbent material. Further, when it employs a coloring reaction (color change), the instrument may not produce sufficient coloring since the contact efficiency is poor.

In the case of the instrument of WO9703209, downpushing of the swab needs to be interrupted for the reaction of the swab with an extracting agent. However, it does not have an interrupting mechanism, though an indicator is provided. Thus, this must be relied on an operator's careful attendance.

The instrument of WO9723596 is assembled into an integral form. Consequently, it may be used only for a coloring reaction and thus lacks a diversity of application.

SUMMARY OF THE INVENTION

Accordingly, the present inventors have continued with studies and found that by enabling removable attachment of a reactive reagent, it can be used as a bacteria collecting member, and that by arranging a container for, e.g., an extracting liquid, to be oriented downwardly and tapered, or by providing swab tip scratching pieces formed by slitting, a cotton swab is held stationary thereat temporarily so that bacteria adhered to the swab can be effectively extracted from the swab and dropped into a reactive reagent container, thereby enabling detection of bacteria. This has lead to the present invention.

According to a first aspect of the present invention, there is provided a sample collecting member comprising: a tubular main body having both upper and lower ends thereof opened; a sample wiping member composed of a retaining member removably fitted into an upper open part of the main body, and a cotton swab held by the retaining member; and an extracting liquid container disposed below the main body.

For preventing the extracting liquid from splashing, a splash-proofing member is desirably provided at a lower part of the main body and below the extracting liquid container.

According to a second aspect of the present invention, there is provided a wipe inspecting instrument comprising: a tubular main body having both upper and lower ends thereof opened, and including a splash-proofing member disposed at a lower part of the main body; a sample wiping member composed of a retaining member removably fitted into an upper open part of the main body, and a cotton swab held by the retaining member; an extracting liquid container disposed above the splash-proofing member; and a reactive reagent container having a test tube shape and so inserted into a lower open part of the main body as to be capable of moving up and down.

In this wipe inspecting instrument also, the splash-proofing member for preventing splashing of the extracting liquid is disposed at the lower part of the main body and below the extracting liquid container.

According to a third aspect of the present invention, there is provided a wipe inspecting instrument comprising: a tubular main body having both upper and lower ends thereof opened, and including a splash-proofing member disposed at a lower part of the main body; a sample wiping member composed of a retaining member removably fitted into an upper open part of the main body, and a cotton swab held by the retaining member; an extracting liquid container disposed above the splash-proofing member; a breaker disposed above the extracting liquid container; and a reactive reagent container having a test tube shape and so inserted into a lower open part of the main body as to be capable of moving up and down.

By providing below the extracting liquid container swab tip ripoff pieces formed by radial slits, it becomes possible to scratch a surface of a tip of the swab and to squeeze the swab, thereby enabling effective bacteria extraction. It is desirable for each swab tip ripoff piece to have a constricted portion at a proximal end thereof.

On an inner wall of the breaker, a movable piece may be provided for facilitating breakage of the seal material. The movable piece is designed to be easily flexed when pressed downwardly by the swab tip.

According to a fourth aspect of the present invention, there is provided a wipe inspecting instrument comprising: a cylindrical connecting member having both upper and lower ends thereof opened, a partition wall provided at an intermediate portion thereof, and a communicating passage extending through the partition wall; a cylindrical main body having both upper and lower ends opened, and including an extracting liquid container disposed at a lower part of the main body, the main body being removably fitted into an upper open part of the connecting member; a sample wiping member removably fitted into an upper open part of the main body, the sample wiping member being composed of a retaining member and a cotton swab held by the retaining member; and a reactive reagent container having a test tube shape and so inserted into a lower open part of the main body as to be capable of moving up and down.

In the arrangement according to the fourth aspect of the invention, a breaker may be provided at a lower part of the main body.

In the instruments according to the second, third and fourth aspects of the present invention, the reactive reagent container may include a measurement container having a lower space portion formed into a polygonal tube, the space portion having opposite sides with outer peripheral portions cut off and separate opposed sides formed into a bulged arc shape so that the separate opposed sides perform a convex lens function.

BEST MODE FOR CARRYING OUT THE INVENTION

Figure 1:
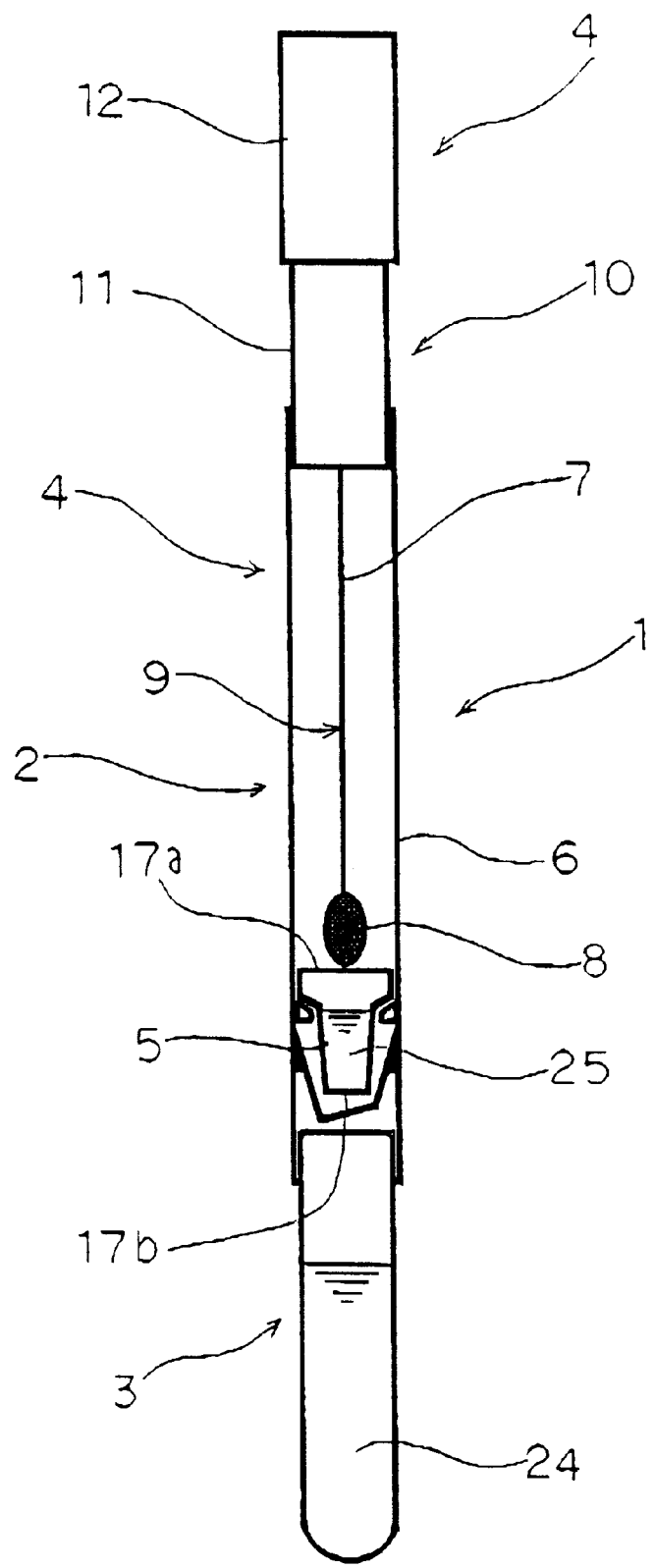
FIG. 1 is a front cross-sectional view of a wipe inspecting instrument according to one embodiment of the present invention.
Figure 2:
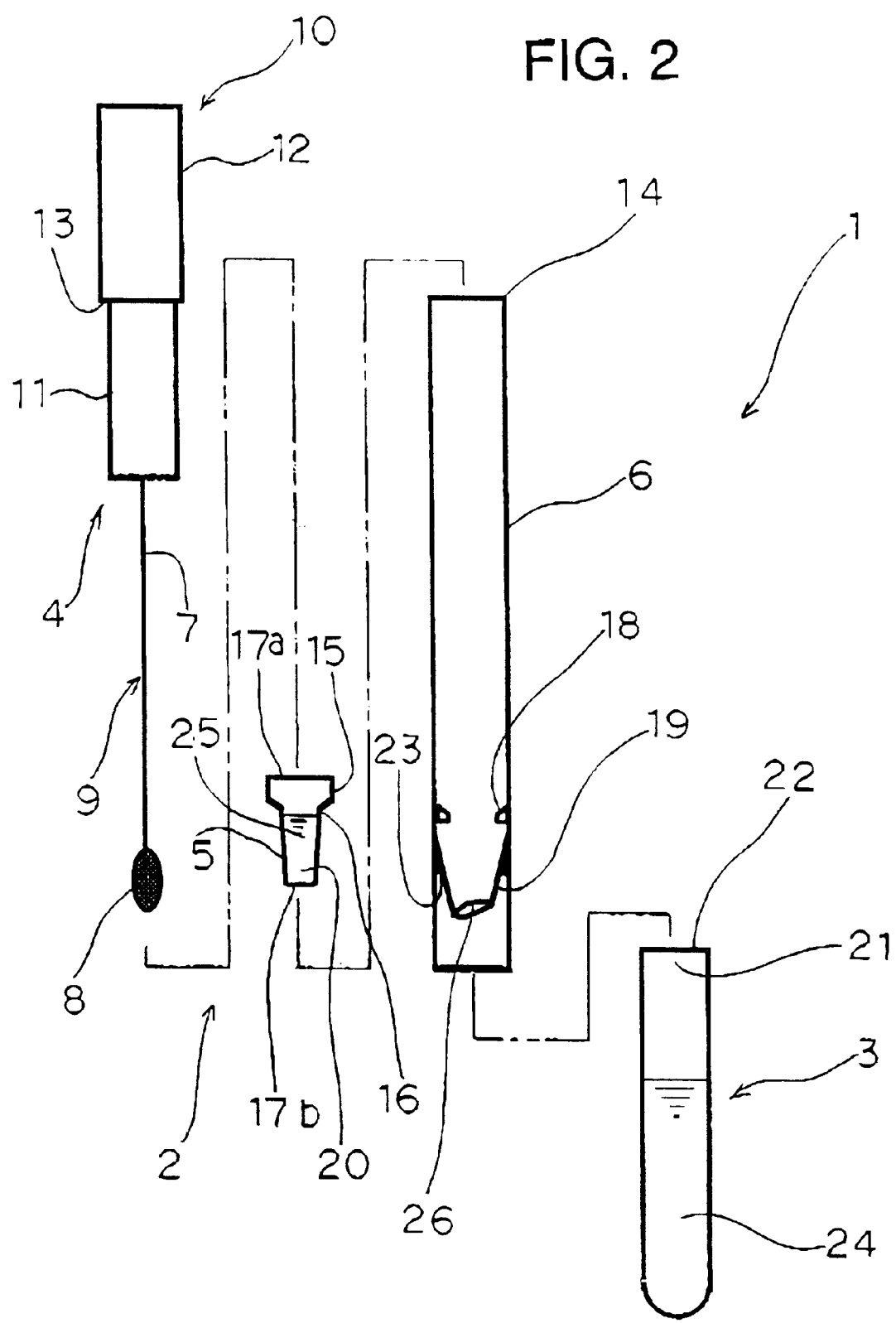
FIG. 2 is an exploded view of the wipe inspecting instrument shown in FIG. 1.

Referring initially to FIGS. 1 and 2, a wipe inspecting instrument according to the present invention, generally designated by reference numeral 1, comprises a sample collecting member 2 and a reactive or test reagent container 3 in the form of a test tube. The sample collecting member 2 is composed of a sample wiping member 4, an extracting liquid container 5 and a tubular main body 6.

Sample wiping member 4 comprises a cotton swab 9 composed of a rod 7 and an egg-shaped cotton bud or tip 8 provided at a lower end thereof, and a retaining member 10 for retaining the swab 9.

Retaining member 10 comprises a lower reduced diameter portion 11 and an upper increased diameter portion 12. The reduced diameter portion 11 has a diameter set so that upon insertion into the main body 6, it can be frictionally held at an elected position. The retaining member 10 also has a stepped portion 13 that acts as a stop by abutting against an upper end 14 of the main body 6.

Sample wiping member 4 is removably fitted into the main body 6 so that it can be removed from the main body 6 to allow wiping of a sample surface with the swab 9 to thereby take bacteria from the surface.

In an extracting liquid container 5, there is preserved in a sealed fashion an extracting liquid 25 or pure water for extracting bacteria stuck to the tip 8 of the swab 9 upon wiping of the sample surface.

Extracting liquid container 5 has a cylindrical upper portion and a conical lower portion which are integrally connected together via a stepped portion 16. The container 5 is thus funnel-shaped. Upper and lower ends of the container 5 are opened to allow injection of an extracting liquid 25. After the container 5 is filled with the liquid 25, the opened upper and lower ends are sealed by seal materials 17a, 17b such as aluminum foil.

Seal materials 17a, 17b should be torn easily by pressing the swab 9. The cylindrical portion 15 of the extracting liquid container 5 has an outer diameter selected so that it can be press inserted deep into the main body 6 easily.

Main body 6 of the sample collecting member 2 is comprised of a tubular member opened at its upper and lower ends. On an inner wall of a lower part of the body 6, there are provided an annular projection 18 and a funnel-shaped splash-proofing member 19. The projection 18 engages with the stepped portion 16 of the extracting liquid container 5 so that the container 5 can be held in position within the body 6.

Annular projection 18 may be omitted when the extracting liquid container 5 is fixed within the main body 6 by means of an adhesive or through fuse connection using heat.

Lower opening 20 of the extracting liquid container 5 has a diameter substantially equal to a lateral diameter (in a direction normal to the swab rod) of the tip or cotton bud 8. As a result, after the seal materials 11a, 17b of the extracting liquid container 5 are tear broken by the swab 9, the tip 8 of the swab 9 is fitted in the opening 20 of the container 5 to thereby close the opening. This guarantees contact of the cotton bud 8 with the extracting liquid, thereby facilitating extraction of bacteria.

Feed of the extracting liquid down into the reagent container 3 may be effected by inwardly pressing that part of the main body 6 where the liquid container 5 is held, or by lightly shaking the main body 6. In the former case, the extracting liquid container 5, main body 6 and splash-proofing member 19 may be formed from flexible materials.

Reactive reagent container 3 has an upper opening 21 which is sealed by a seal material such as aluminum foil after the reagent container 3 is filled with a reactive reagent such as a coloring reagent. In this state, the reactive reagent container 3 is then inserted into the main body 6 from below. Consequently, the reactive reagent container 3 has an outer diameter selected so that it, upon insertion into the main body 6, stops at an elected position by frictional contact with the inside of the main body 6.

By pushing the reactive reagent container 3, the seal material 22 is torn by an opening 26 of the splash-proofing member 19, whereupon bacterial extracted from the swab tip 8 flows with the extracting liquid down into the reactive reagent container 3 to cause a coloring reaction in the reactive reagent contained in the reagent container 3 so that the bacteria can be detected.

Opening 26 may be acute-angled, as shown in FIG. 2, so that it can tear the seal material 22 effectively.

Reactive (test) reagent may be one combination of luciferase, luciferin, magnesium ions, dithiothreitol and a buffer, or another combination of luciferase, dithiothreitol, pyruvateorthophosphate dikinase, phosphenol pyruvic acid, sodium pyrophosphate, luciferin, magnesium ions and a buffer.

Wipe inspecting instrument 1 is commercially distributed with the reduced diameter portion 11 of the sample wiping member 4 and the reactive reagent container 3 fitted halfway into the main body as shown in FIG. 1. At this time, the extracting liquid container 5 and the reactive reagent container 3 are filled respectively with an extracting liquid and a reactive reagent and sealed by the respective seal materials 17a, 17b, 22.

Figure 3:
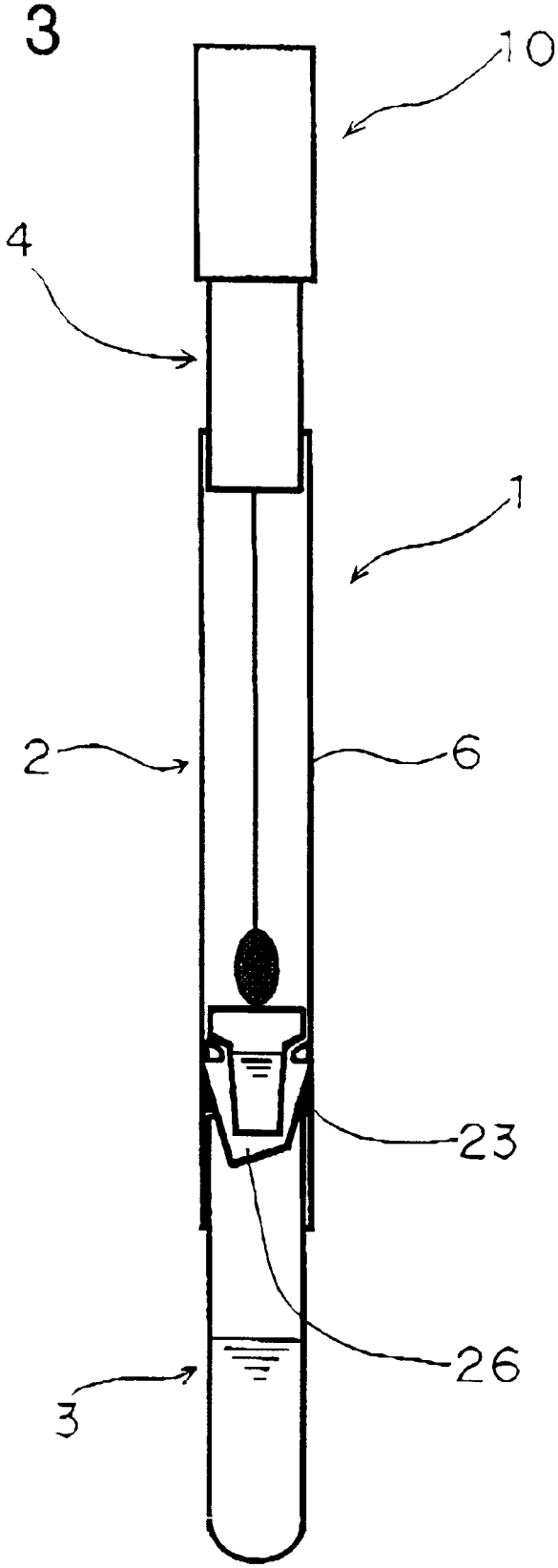
FIG. 3 is a view with a reactive reagent container of the wipe inspecting instrument shown in an elevated position.

In use, the sample wiping member 4 is pulled out of the main body 6. Then, a sample surface is wiped with the swab tip 8 to take bacteria. Thereafter, the sample wiping member 4 with the collected bacteria is inserted into the main body 6, following which the reactive reagent container 3 is pushed up until the seal material 22 of the container 3 is abutted against and ruptured by the opening 26 of the splash-proofing member 19. At this time, a junction 23 between the splash-proofing member 19 and the main body 6 serves as a stop so that the reactive reagent container 3 always stops at a given position, as shown in FIG. 3.

Figure 4:
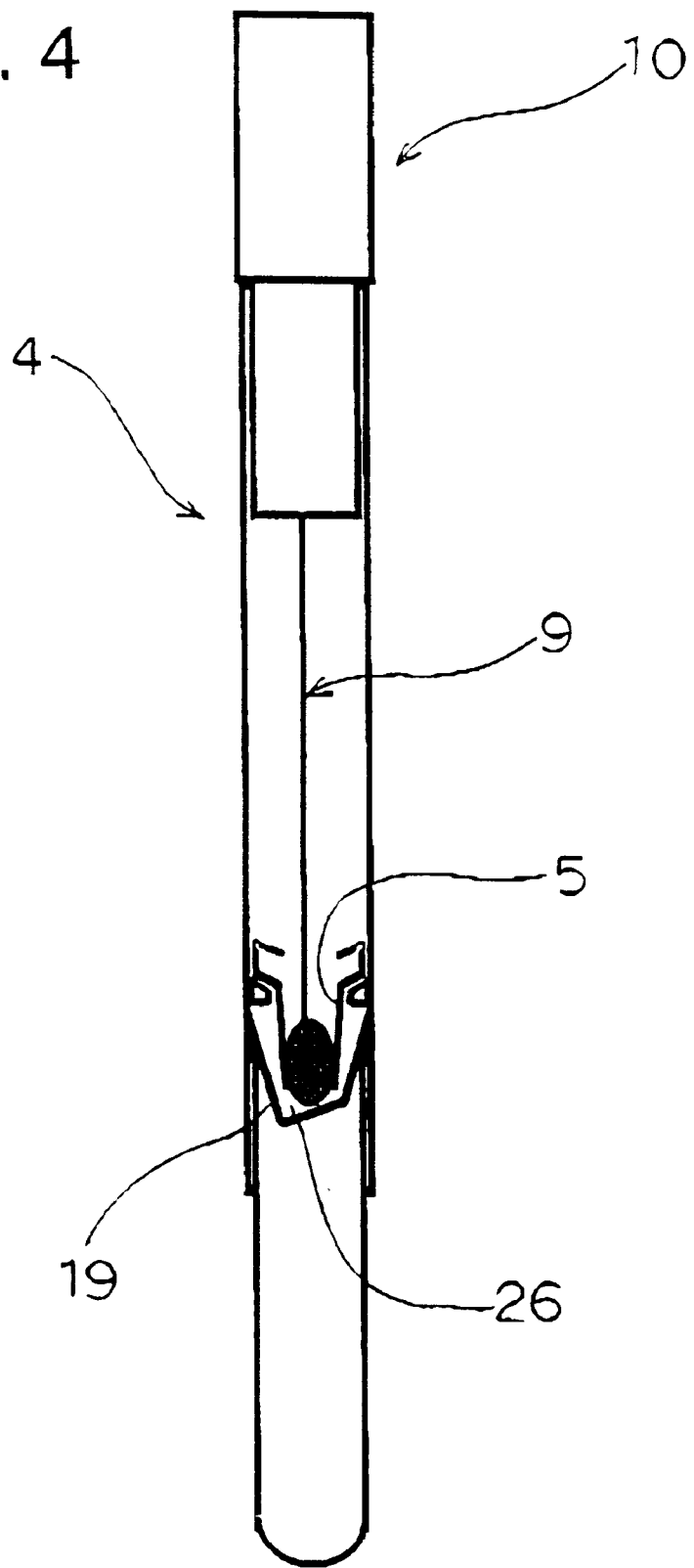
FIG. 4 is a view with the reactive reagent container shown in a lowered position.

Next, the sample wiping member 4 is pushed down until the stepped portion 13 of the retaining member 10 and the upper end 14 of the main body 6 are placed in abutting engagement as shown in FIG. 4.

This causes the upper and lower seal materials 17a, 17b to be ruptured one after another by the swab 9 so that the bacterial stuck to the cotton bud 8 is transported to the extracting liquid upon contact therewith. For this purpose, the sample wiping member 4 is arranged so that the swab tip 8 is positioned to cover the opening 20 of the extracting liquid container 5 when the stepped portion 13 of the retaining member 10 is abutted against the upper end 14 of the main body 6.

By arranging the opening 20 of the extracting liquid container 5 with the swab tip 8, as explained above, required time contact of the tip 8 with the extracting liquid is achieved.

Continuously, that portion of the main body where the extracting liquid container is positioned is squeezed, whereupon the tip 8 is also squeezed indirectly. This causes the opening 20 to become oval-shaped to facilitate drop of the extracting liquid into the reagent container 3, whereby the extracting liquid containing the bacteria is contacted with the reagent 24. As a result, the content of the reagent container 3 radiates light due to a coloring reaction occurring therein. Finally, the reagent container 3 is attached to a luminometer to measure the quantity of the radiated light and hence the quantity of the bacteria.

Upon the above described squeezing operation, splashing of the extracting liquid is prevented by the splash-proofing member so that whole extracting liquid is fed into the reagent container 3.

Figure 5:
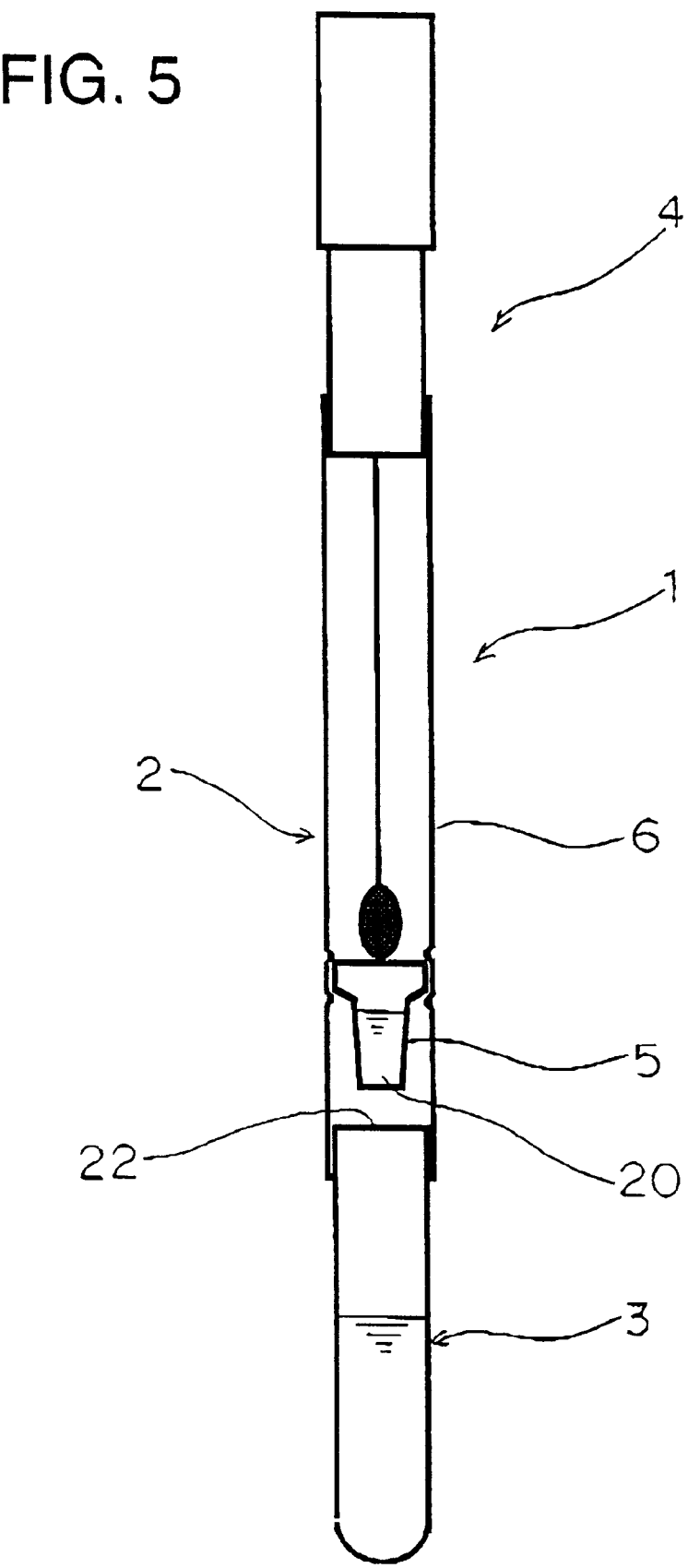
FIG. 5 is a front cross-sectional view of a wipe inspecting instrument according to another embodiment of the present invention.

Reference is made next to FIG. 5 illustrating another embodiment of the invention. This embodiment differs from the above described embodiment described above in that the splash-proofing member 19 is omitted. In the illustrated embodiment, the extracting liquid container 5 is fixed to the main body 6 and the seal material 22 of the reactive reagent container 3 is broken by the opening 20 of the container 5. In this embodiment, squeezing of the main body 6 and the internal extracting liquid container 5 should be performed slowly so that splashing of the extracting liquid can be avoided and whole liquid can be fed to the reactive reagent container 3.

In the embodiment just described, the extracting liquid container 5 is secured directly to the main body 6.

Figure 6:
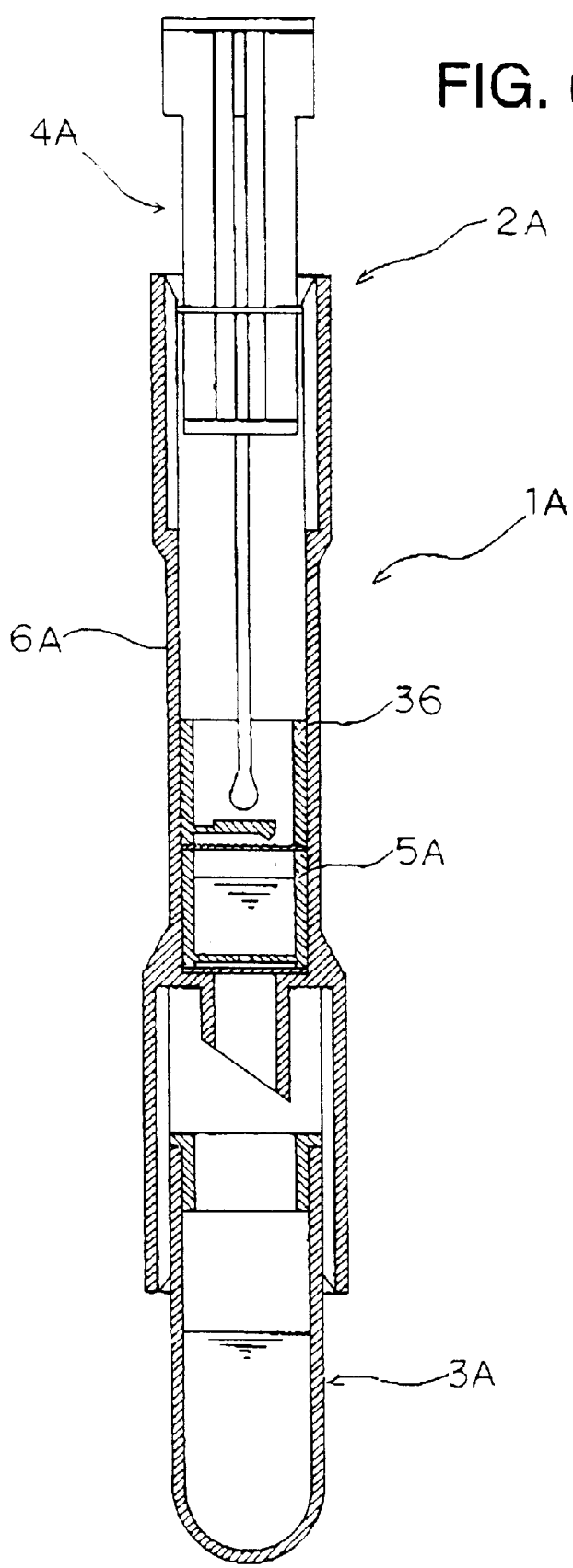
FIG. 6 is a front cross-sectional view of a wipe inspection instrument according to still another embodiment of the present invention.
Figure 7:
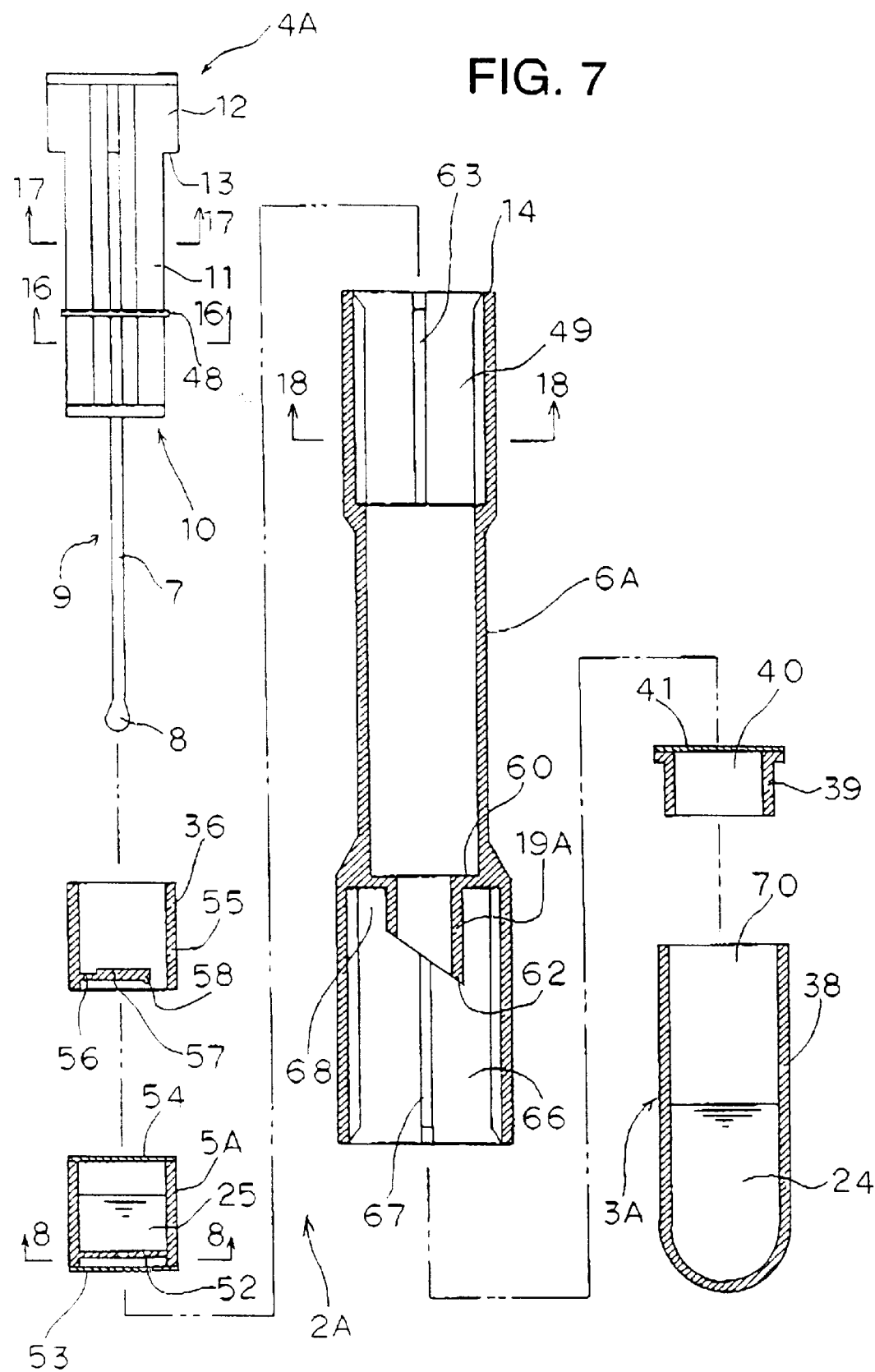
FIG. 7 is an exploded view of the wipe inspecting instrument shown in FIG. 6.

Discussion will be made next as to other embodiments of the invention with reference to FIGS. 6 to 18. As shown in FIGS. 6 and 7, a wipe inspecting instrument, generally designated by reference numeral 1A, comprises a sample collecting member 2A and a reactive reagent container 3A in the form of a test tube. The sample collecting member 2A comprises a sample wiping member 4A, an extracting liquid container 5A, a breaker 36 and a tubular-shaped main body 6A forming major part of the sample collecting member 2A.

Reactive reagent container 3A is comprised of a measurement container 38 and a cylindrical cap 39 with upper and lower sides opened. Particularly, the upper opening 40 is closed by, for example, a seal material 41 of aluminum foil. The reactive reagent container 3A is sealed by attachment of the cap 39 thereto.

Sample wiping member 4A is comprised of a cotton swab 9 composed of a rod 7 and an egg-shaped cotton bud or tip 8 at a lower end thereof, and a retaining member 10 for retaining the swab 9.

Figure 16:
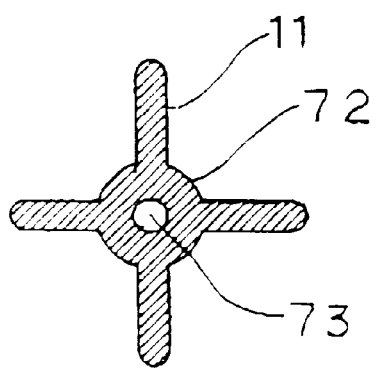
FIG. 16 is a cross-sectional view taken along line 16—16 of FIG. 7.
Figure 17:
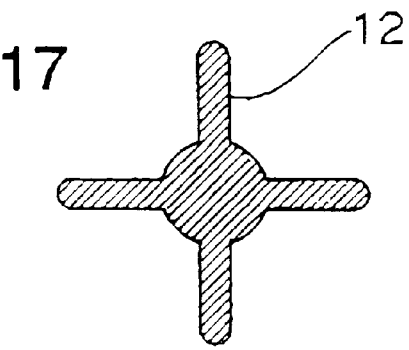
FIG. 17 is a cross-sectional view taken along line 17—17 of FIG. 7.

Retaining member 10 is comprised of a lower reduced diameter portion 11 and an upper increased diameter portion 12. For making it light in weight and easy to handle, the retaining member 10 has a cross-shaped section, as shown in FIGS. 16 and 17. The reduced diameter portion 11 has a brim-shaped member 48 provided at a nearly mid-part thereof, a diameter of which is a diameter of the reduced diameter portion 11. The brim-shaped member 48 is flexible in a direction of the rod and has an outer diameter slightly larger than an inner diameter of an inserting part of the reduced diameter portion 11 of the main body 6A. In this arrangement, when the reduced diameter portion 11 is inserted into the main body 6A, the brim-shaped member 48 deforms slightly to produce a moderate resistive force so that the sample wiping member 4A can be fixed at an elected position in the main body 6A.

When the sample collecting member 4A moves down within the main body 6A, a stepped portion 12 bordering the reduced and increased diameter portions 11, 12 abuts against an upper end 14 so that the sample collecting member 4A stops at a given position.

Sample collecting member 4A is removably fitted in the main body 6A so that it can be pulled out from the main body 6A for taking bacteria by wiping a sample surface with the swab 9.

In the extracting liquid container 5A, there is preserved in a sealed fashion an extracting liquid 25 or pure water for extracting bacteria stuck to the swab tip 8 upon wiping a sample therewith.

Figure 8:
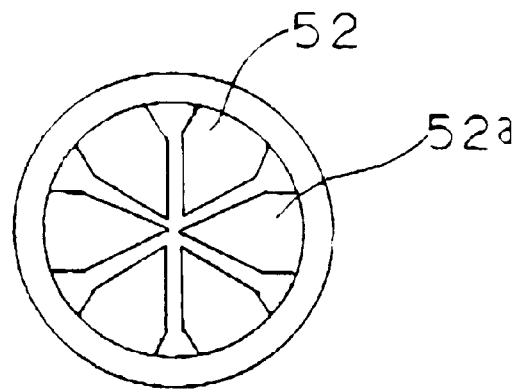
FIG. 8 is a view taken in the direction of arrow 8—8 of FIG. 7.
Figure 11:
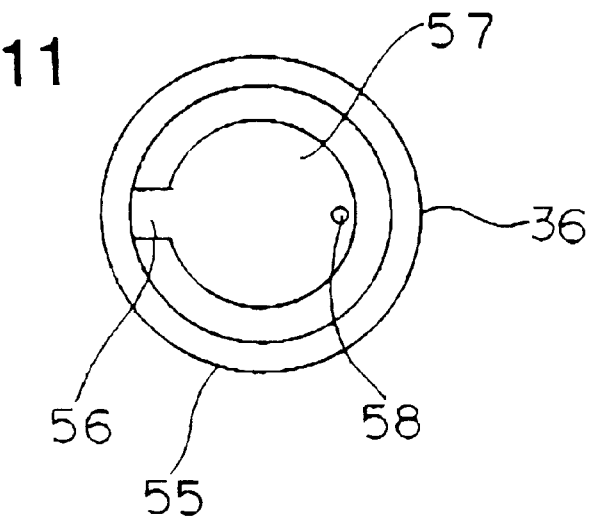
FIG. 11 is a bottom view of a breaker.

Extracting liquid container 5A is formed cylindrically and has at a lower part thereof radial slits to provide cotton bud ripoff or scratching pieces 52 as shown in FIG. 8. The container 5A is opened at upper and lower ends thereof. After the lower end is sealed by a seal material 53, the extracting liquid 25 is poured into the container 5A. This is followed by sealing the upper end with a seal material 54 to thereby preserve liquid 25 in the container 5A in a sealed fashion.

Seal materials 53, 54 may be formed from such materials as aluminum foil that can be easily ruptured by pressing contact of the swab 9. An outer diameter of the cylindrical part of the extracting liquid container 5A may be set to permit easy insertion into the main body 6A.

With the radial slits, the tip ripoff pieces 52 of the extracting liquid container 5A can be flexed to be spread open, as if petals bloom, by the swab tip 8 pierced past the seal material 54 on the upper part of the container 5A, as discussed in detail below. At this time, pointed tips of the ripoff pieces 52 rupture the lower seal material 53 of the container 5A and serve to position the swab tip 8 centrally of the container 5A. By virtue of this arrangement, the extracting liquid and the cotton bud 8 can be surely contacted with each other. In addition, since the pointed tips scrub a surface of the cotton bud 8 and squeeze the bud 8 as the latter passes therethrough, bacteria can be effectively extracted.

One pair 52a among the illustrated three pairs of the ripoff pieces 52 may desirably be longer than the other pairs, that is, extend closer to the center of the container 5A, as shown in FIG. 8. AS a result, the ripoff pieces 52a contact the seal material 53 first, whereby the seal material 53 can be ruptured with smaller force owing to the principle of stress concentration.

Figure 9:
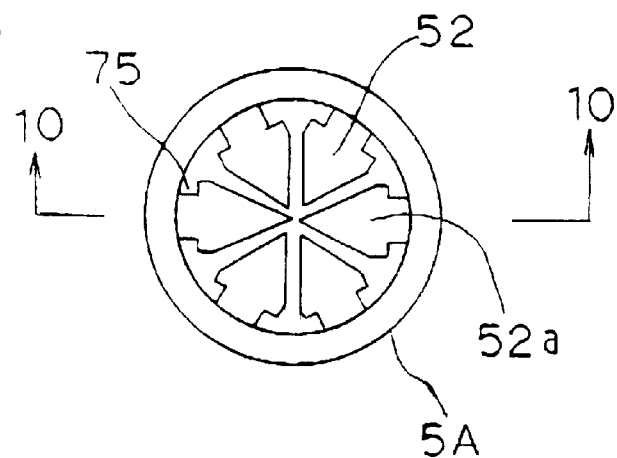
FIG. 9 is a view showing a modified extraction liquid container.

Reference is made next to FIG. 9 illustrating a further embodiment of the tip ripoff pieces 52. In this embodiment, the ripoff pieces 52 have constricted portions 75 at proximal ends thereof. With this arrangement, the tip ripoff pieces 52 can be flexed easily.

Figure 10:
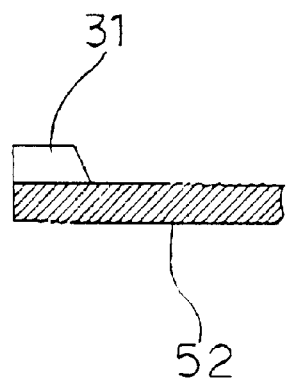
FIG. 10 is a cross-sectional view taken along line 10—10 of FIG. 9.

Swab tip ripoff pieces 52 may be provided at their top ends with cutting blades 31, as shown in FIG. 10, so that seal material rupture can be achieved more effectively.

At a lower part, the breaker 36 has a movable piece 57 with one end connected via a connector piece 56 to an inner wall of a body part 55 thereof. The movable piece 57 is designed to flex easily when pushed downwardly by the swab tip 8 (see also FIG. 11). On a lower side of its top end, the movable piece 57 also has a sharp-edged projection 58 for effectively rupturing the seal material 54. The breaker 36 is not always required to be provided; it may be omitted when the seal material 54 can be ruptured easily by the swab 9.

Figure 12:
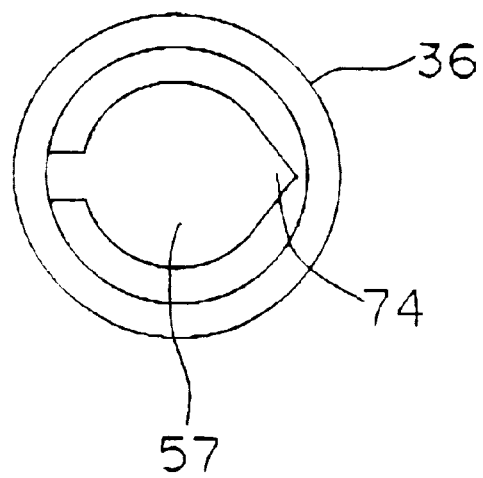
FIG. 12 is a bottom view showing a modification of the breaker.

Reference is made next to FIG. 12 illustrating a still further embodiment. This embodiment is characterized in that the movable piece 57 is provided with an acute-angled or sharp cutting blade 74 on a lower side of its top end.

Figure 13:
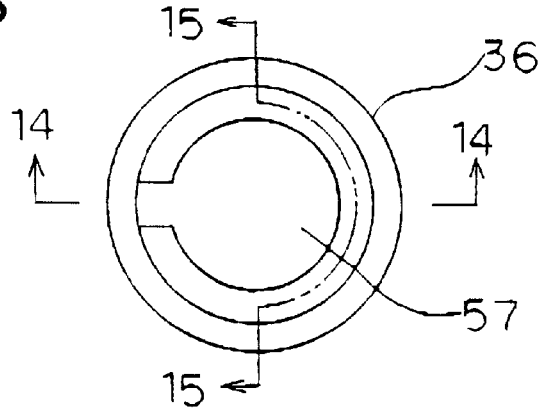
FIG. 13 is a bottom view showing another modification of the breaker.
Figure 14:
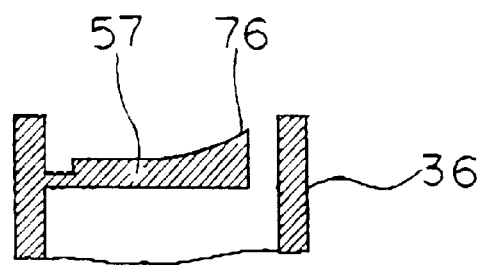
FIG. 14 is a cross-sectional view taken along line 14—14 of FIG. 13.
Figure 15:
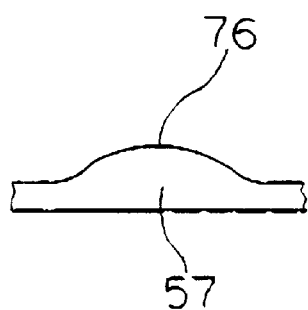
FIG. 15 is a cross-sectional view taken along line 15—15 of FIG. 13.

In FIGS. 13 to 15, a still further embodiment is illustrated. This embodiment is characterized by a cutting blade 76 provided on a lower side of its top end.

In place of the movable piece 57 of the breaker 36, the tip ripoff pieces 52 as shown in FIGS. 8 and 9 may be used.

Main body 6A of the sample collecting member 2A is comprised of a tubular member opened at upper and lower ends thereof and has an annular projection member 60 provided on a lower inner wall surface thereof. The projection member 60 has a splash-proofing member 19A extending downwardly therefrom. The extracting liquid container 5A is placed on the projection member 60, whereby the container 5A is held at a given position within the main body 6A.

When the extracting liquid 25 containing the extracted bacteria from the swab tip 8 is fed to the reactive reagent container 3A, the splash-proofing member 19A not only prevents splashing of the extracting liquid 25 but also works to rupture the seal material 41 of the cap 39. For this reason, a lower end of the splash-proofing member 19A has an acute-angled portion 62 formed by slicing the member aslant.

Figure 18:
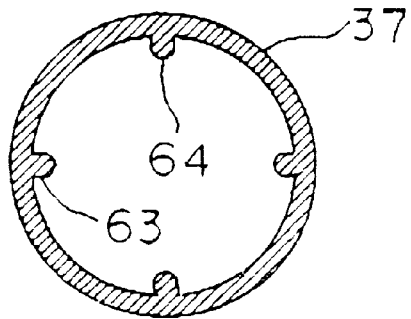
FIG. 18 is a cross-sectional view taken along line 18—18 of FIG. 7.

Upper end of the main body 6A, that is, the inserting part 49 for the sample wiping member 4A has on its inner wall linear projection members 63 extending axially of the body 6A (see also FIG. 18). Upon insertion of the sample wiping member 4A into the inserting part 49 of the main body 6A, an outer periphery of the brim-shaped member 48 slides on tops 64 of the projection members 63. The sliding movement becomes smooth, because an area of frictional contact is made small by the provision of the projection members 63. To further facilitate insertion of the brim-shaped member 48 into the inserting part 49, an inlet of the inserting part 49 is tapered.

Lower end of the main body 6A, that is, inserting part 66 for the reactive reagent container 3A is also provided with linear projection members 67. Between the splash-proofing member 19A and an inner wall surface of the main body 6A, there is defined a ring-shaped clearance 68. The reactive reagent container 3A is inserted in that clearance for rupturing the seal material 41. At this time, the projection member 60 acts as a stop for the reactive reagent container 3A.

Feed of the extracting liquid 25 into the reagent container 3A is carried out by squeezing the splash-proofing member 19A or by lightly shaking the main body 6A after the same is faced down. Consequently, in the former case, the extracting liquid container 5A, main body 6A and splash-proofing member 19A are formed from a flexible material.

After the measuring container 38 is fed with a reactive reagent 24 such as a coloring reagent, an upper opening 70 of the reactive reagent container 3A is sealed by the cap 39 which in turn is sealed at its upper end by the seal material 41. In this state, the reactive reagent container 3A is inserted into the main body 6A from below. Thus, the reactive reagent container 3A has an outer diameter designed such that upon insertion into the main body 6A, the container 3A stops at an elected position by friction.

Upward thrusting of the reagent container 3A causes the seal material 41 to be ruptured by the acute-angled portion 62 of the splash-proofing member 19A. As a result, the bacterial extracted from the swab tip 8 drops along with the extracting liquid down into the reagent container 3A for subsequent coloring reaction and bacteria detection.

Wipe inspecting instrument 1A is commercially distributed in such a form as shown in FIG. 6, that is, with the reduced-diameter portion 11 of the sample wiping member 4A and the reagent container 3A inserted halfway into the main body 6A. More specifically, the extracting liquid container 5A and the reagent container 3A are filled respectively with the extracting liquid 25 and the reagent 24 and kept sealed by the respective seal materials 41, 53, 54.

In use, the sample wiping member 4A is firstly pulled out from the main body 6A for wiping with the tip 8 a sample surface to take bacteria. The sample wiping member 4A with the collected bacteria is then inserted into the main body 6A, whereafter the reagent container 3A is pushed up to cause its seal material 41 to be pressed against the acute-angled portion 62 of the splash-proofing member 19A to thereby rupture the seal material 41. At this time, the projection member 60 acts as a stop so that the reagent container 3A is held at a given position.

Next, the sample wiping member 4A is pushed down cause the cotton swab 9 to forcibly flex the movable piece 57 of the breaker 36 and to rupture the upper seal material 54 of the extracting liquid container 5A, until the tip 8 enters into the extracting liquid container 5A.

Figure 19:
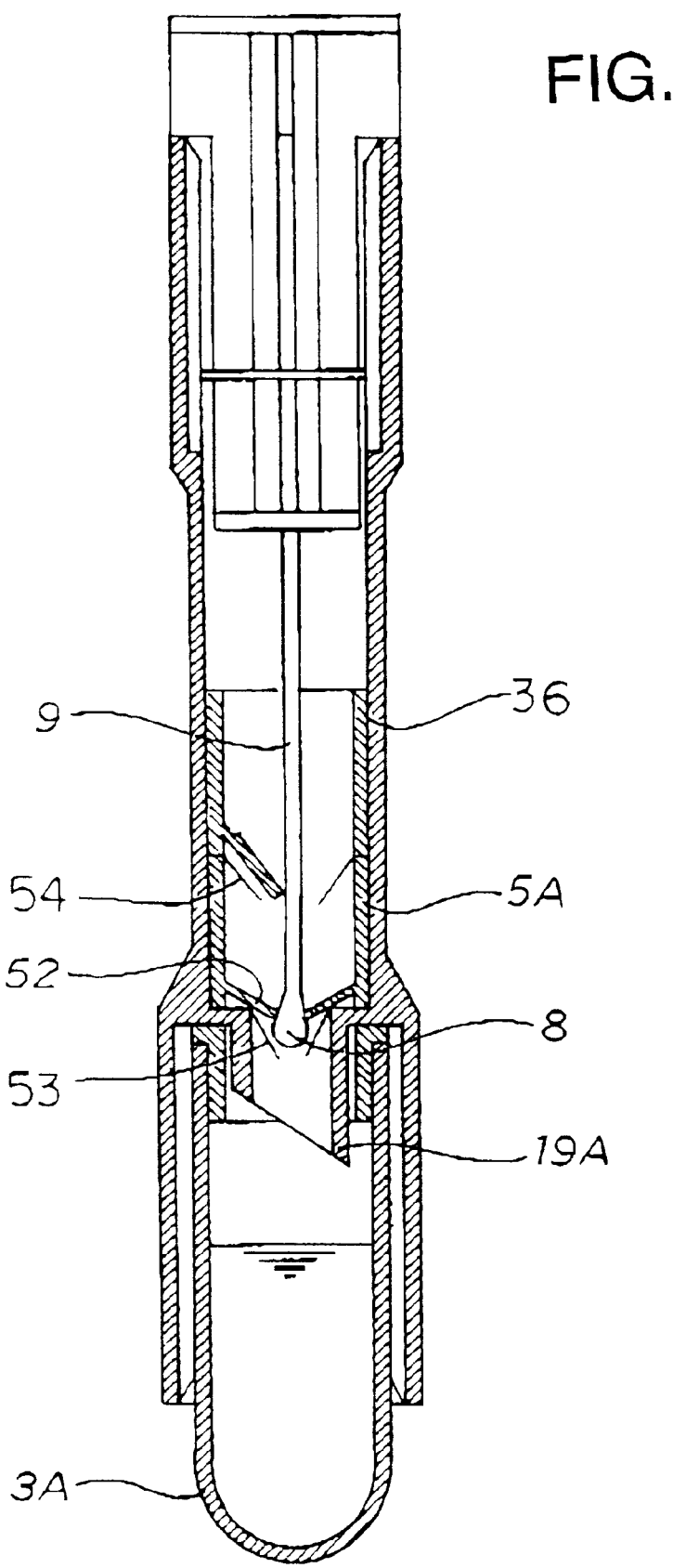
FIG. 19 is a view similar to FIG. 6, showing the condition in which a light-emitting reaction occurs.

Pushing of the sample wiping member 4A is continued until the stepped portion 13 of the retaining member 10 abuts against the upper end 14 of the main body 6A. During this continued pushing of the swab 9, the swab tip 8 is applied with resistance by the tip ripoff pieces 52, whereby prolonged contact of the tip 8 with the extracting liquid 25 and hence effective transport of the bacteria on the swab tip 8 to the extracting liquid 25 are guaranteed. Further, by virtue of the process in which the surface of the swab tip 8 is scratched by the tips of the cotton bud ripoff pieces 52 flex opened, bacterial held on the surface of the cotton bud or swab tip 8 can be efficiently transferred into the liquid (see FIG. 19).

When the seal material 54 of the extracting liquid container 5A is ruptured by the cotton bud ripoff pieces 52 and the swab tip 8, by virtue of the structural arrangement of the ripoff pieces 52, the liquid does not go out of the extracting liquid container 5A instantly, whereby duration of contact of the swab tip 8 with the extracting liquid 25 is prolonged.

Continuously, that portion of the main body 6A where the extracting liquid container 5A is held is squeezed, or the wipe inspecting instrument 1A is lightly shaken vertically, so that the extracting liquid containing the bacteria drops into the reagent container 3A where the reagent 24 and the liquid 25 containing the bacteria are contacted with each other to initiate a coloring reaction which produces light. Finally, the reagent container 3A is attached to a luminometer for measuring the amount of emitted light and hence the amount of the bacteria.

Part of the extracting liquid may splash around during the squeezing operation but this can be prevented by the splash-proofing member 19A so that the extracting liquid is wholly fed to the reagent container 3A.

Figure 20:
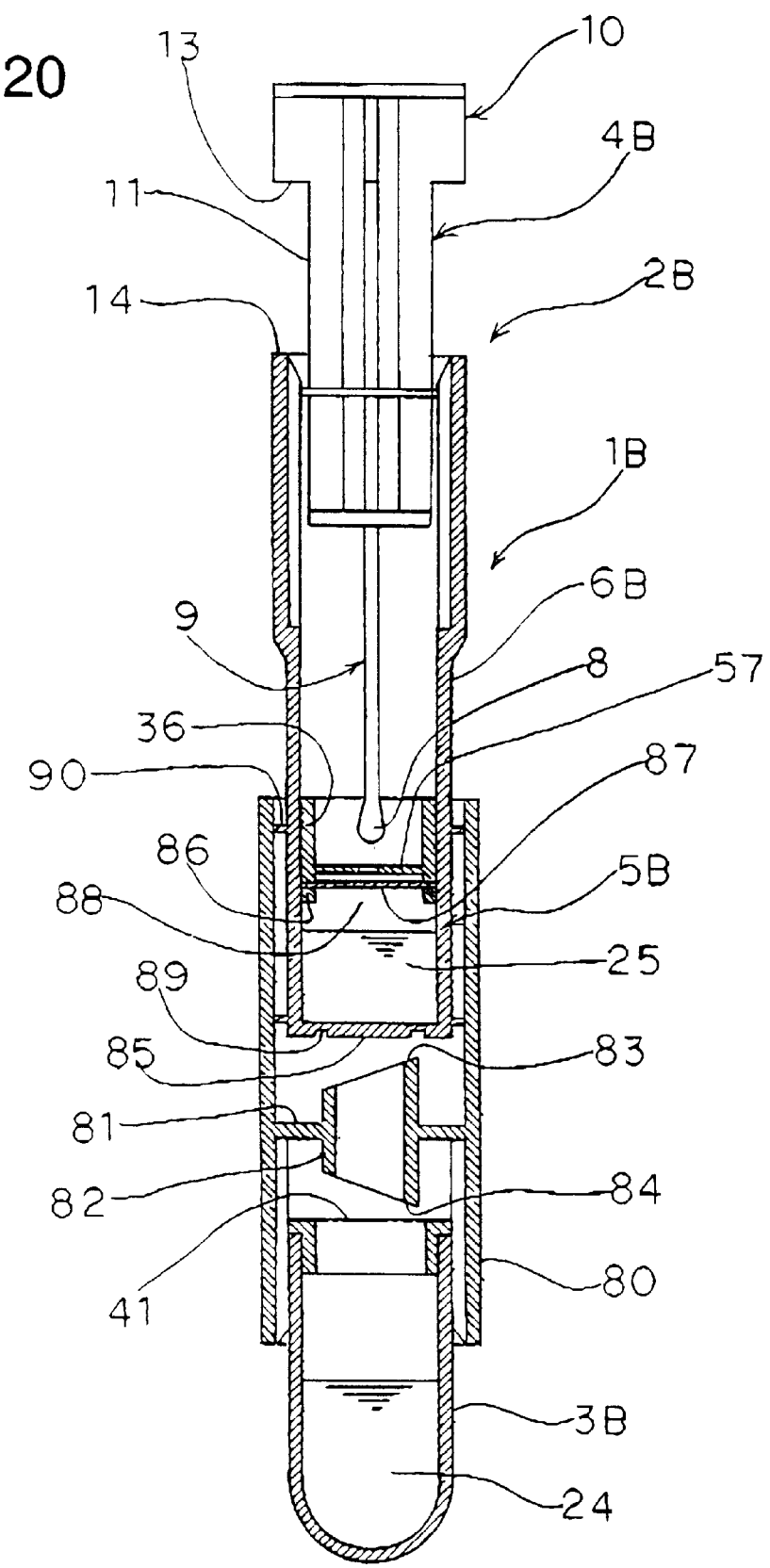
FIG. 20 is a front cross-sectional view of a wipe inspecting instrument according to a further embodiment of the present invention.
Figure 21:
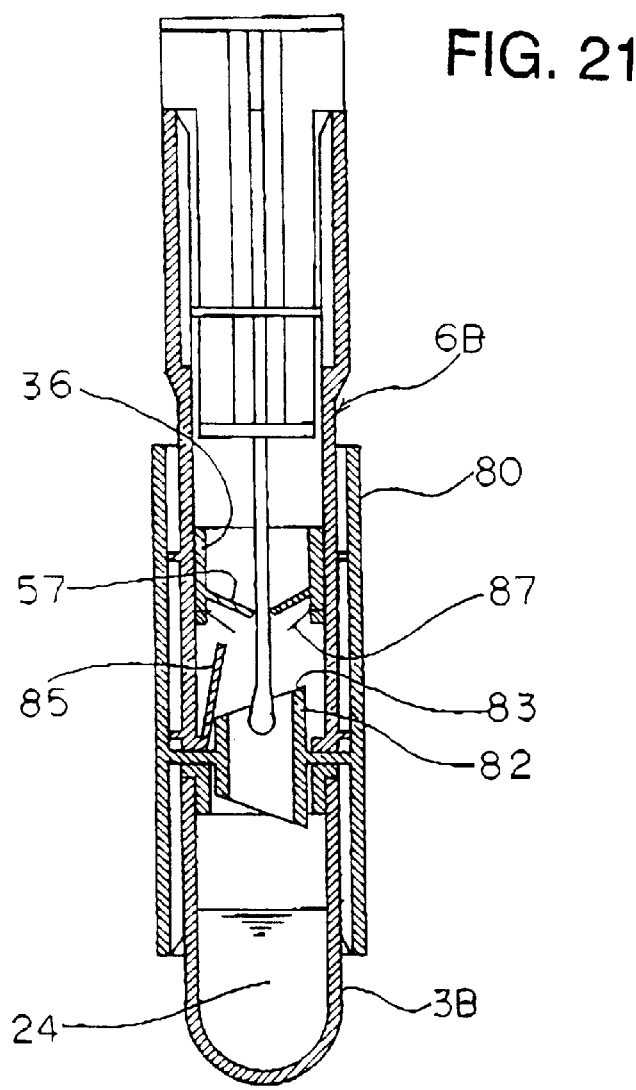
FIG. 21 is a view similar to FIG. 20, showing the condition in which a light-emitting reaction occurs.

Reference is made next to FIGS. 20 and 21 illustrating a still further embodiment. This embodiment is characterized by an extracting liquid container 5B formed integrally with a main body 6B at a lower part of the latter and a connector member 80 with the main body 6B and a reactive reagent container 3B fitted therein.

Connector member 80 is formed cylindrically and has a partition wall 81 at a nearly middle part thereof. In an upper part of the connector member 80, the main body 6B is partly fitted vertically movably. In a lower part of the connector member 80, the reagent container 3B is fitted vertically movably. The main body 6B and the reagent container 3B are unitarily held by the connector member 80 and form part of a wipe inspecting instrument 1B. A sample collecting member 2B is comprised of a sample wiping member 4B and the main body 6B. The sample wiping member 4B is comprised of a cotton swab 9 and a swab retaining member 10.

Partition wall 81 has a communicating passage 82 passing therethrough with acute-angled upper and lower ends 83, 84 for breaking a seal material 41 of the reagent container 3B and a bottom 85 of the main body 6B. The bottom 85 of the main body 6B also serves as the bottom of the extracting liquid container 5B. A breaker 36 is fitted within an upper part of the liquid container 5B and placed on a projection member 86.

Below the breaker 36, a seal material 87 is adhesively secured. Provision of the breaker 36 provides a sealed chamber 88 defined inside a lower end of the main body 6B, in which an extracting liquid 25 is sealingly held. The bottom 85 may be formed thin so that it can be ruptured easily. Otherwise, a ring-shaped cutout 89 may be provided as shown in FIG. 20.

Figure 22:
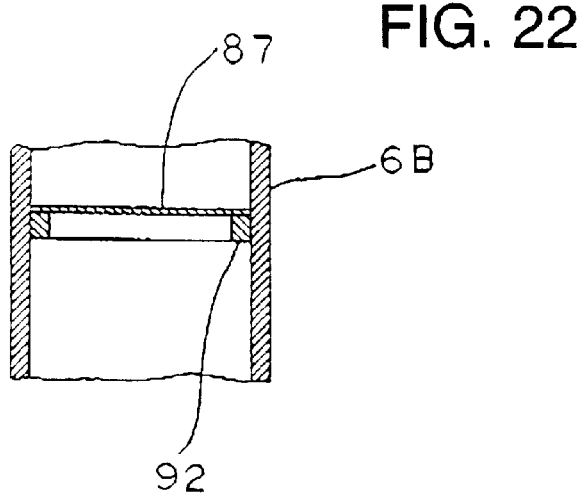
FIG. 22 is an enlarged view showing a modified seal portion.

As can be appreciated from FIG. 22, the breaker 36 may be omitted where the seal material 87 is easily breakable. In this instance, the seal material 87 may be adhesively attached to the ring-shaped projection member 92 within the main body Brim-shaped member 90, slightly larger than an inner diameter of the connector member 80, is provided to extend around an outer periphery of the lower part of the main body 6B, so that the main body 6a, when fitted into the connector member 80, can stop at an elected position. With this arrangement, it becomes possible to prevent the extracting liquid 25 from leaking upon rupture of the bottom 85, even when the wipe inspecting instrument 1 is held upside down.

For assembling the above-described wipe inspecting instrument 1B, the main body 6B is first filled with the extracting liquid, whereafter the breaker 36 with the bottom sealed by the seal material 87 is inserted into the main body 6B to thereby place the extracting liquid in a sealed state. Next, the sample wiping member 4B is inserted into the main body 6B until its swab tip 8 comes closely to the breaker 36.

Then, the main body 6B with the inserted sample wiping member 4B, that is, the sample collecting member 2B is press fitted into the connector member 80 until the bottom 85 of the main body 6B comes closely to the upper end 83 of the communication passage 82. Thereafter, the reactive reagent container 3B is inserted into the lower opening of the connector member 80. This places the instrument 1B in such a condition as shown in FIG. 20.

In use of the wipe inspecting instrument 1B, the sample wiping member 4B is pulled out of the main body 6B for wiping a sample surface with the cotton bud 8 to thereby take bacteria. The sample wiping member 4B carrying the taken bacteria is then fitted into the main body 6B, following which the reagent container 3B is upwardly press moved to cause the seal material 41 of the container 3B to be abutted against the lower end 84 of the communication passage 82 for rupturing the seal 41.

Thereafter, the sample wiping member 4B is pushed down until the stepped portion 13 of the retaining member 10 and the upper end 14 of the main body 6B are abutted against each other. This effects rupture of the seal material 87 by the movable piece 57 of the breaker 36 flexed downwardly by the swab tip 8, whereby the bacteria stuck to the tip 8 is transferred into the extracting liquid through contact with the latter.

Continuously, the main body 6B is pushed down to cause the bottom 85 of the main body 6B to be ruptured by the upper end 83 of the communication passage 82. As a result, the extracting liquid containing the bacteria flows through the communication passage 82 into the reagent container 3B and contacts with the reagent 24 therein. Finally, the presence of the bacterial is confirmed through coloring reaction. This state is as shown in FIG. 21.

Figure 23:
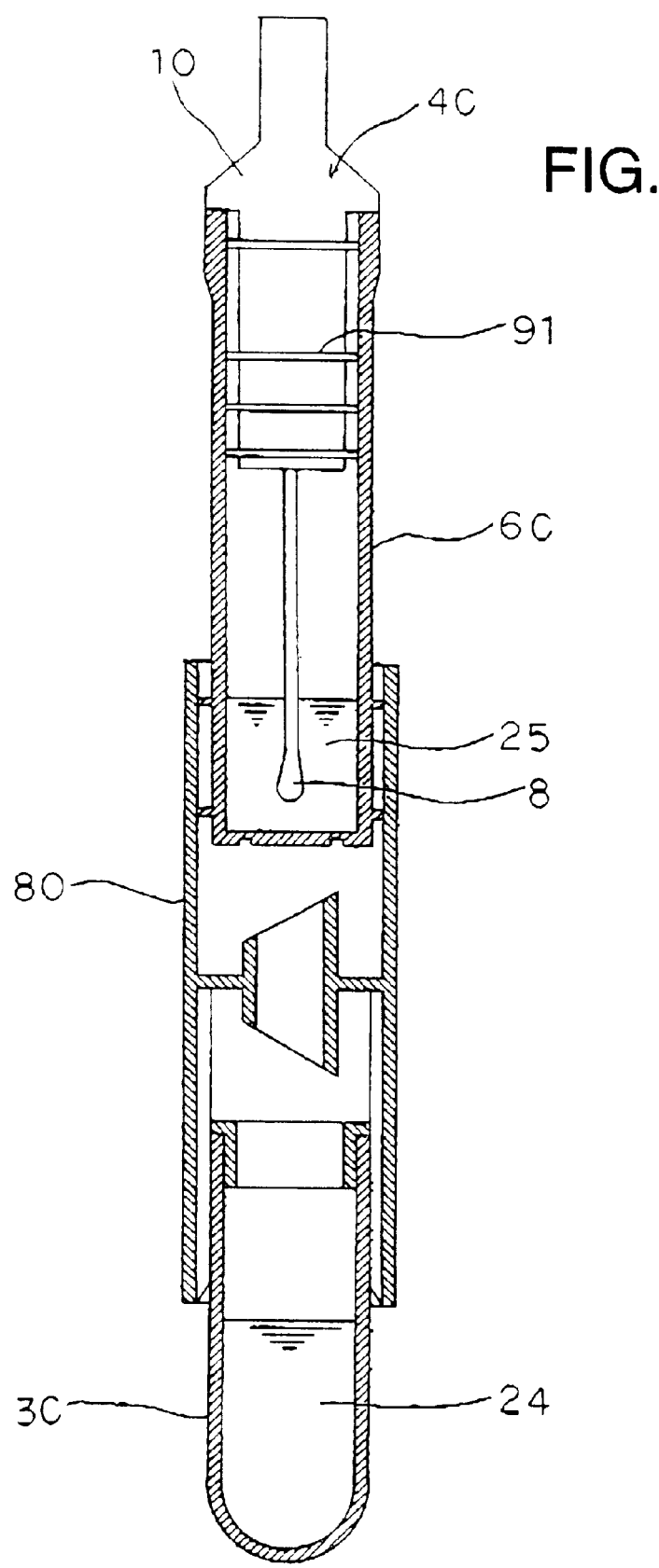
FIG. 23 is a front cross-sectional view of a wipe inspecting instrument according to another embodiment of the present invention.
Figure 24:
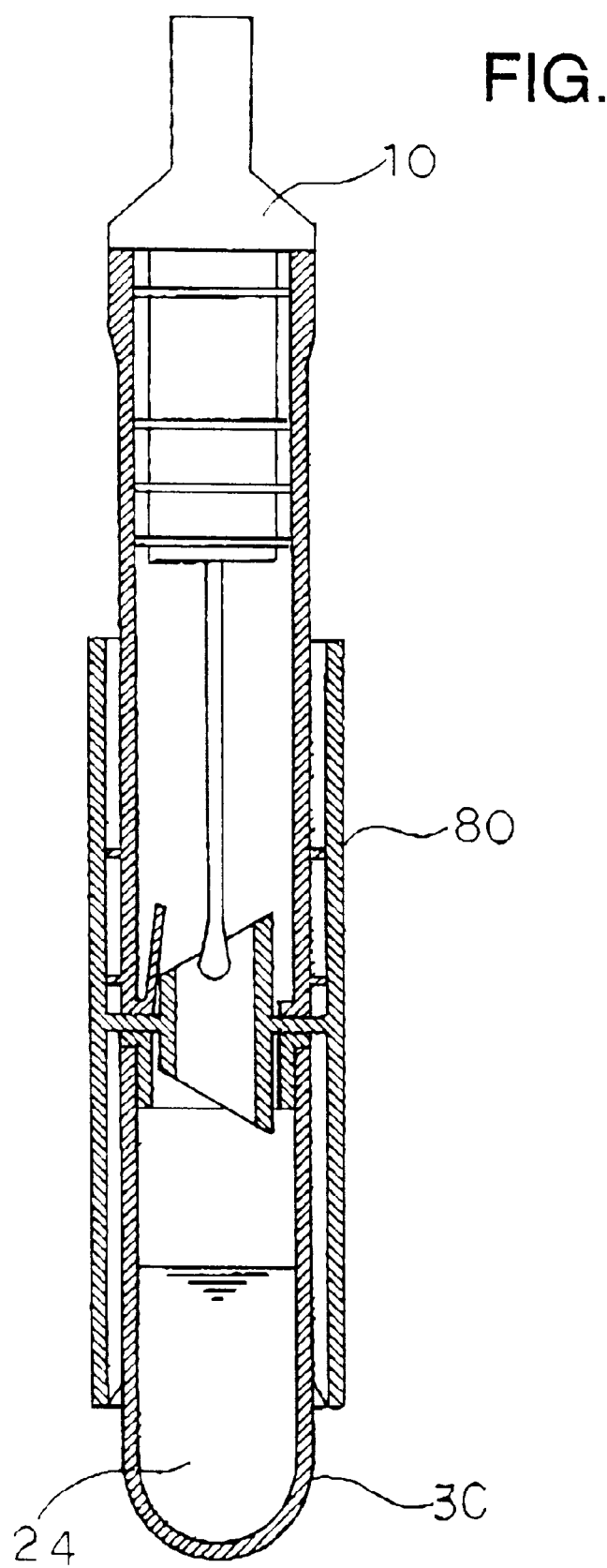
FIG. 24 is a view similar to FIG. 23, showing the condition in which a light-emitting reaction occurs.

Reference is made next to FIGS. 23 and 24 illustrating a still further embodiment. This embodiment differs from the embodiment of FIGS. 20 and 21 in that it lacks the breaker 36. In the embodiment being described, the extracting liquid 25 is sealed in a main body 6C. Thus, the swab tip 8 is held in contact with the extracting liquid prior to use.

Retaining member 10 of a sample wiping member 4C is provided with a brim-shaped member 91. Thus, when the wiping member 4C is inserted into the main body 6C, a sealed state is established within the main body 6C. FIG. 23 shows a prior-to-use state of the illustrated instrument while FIG. 24 illustrates a state in which the extracting liquid containing bacteria is held in contact with a luminous reagent.

Figure 25:
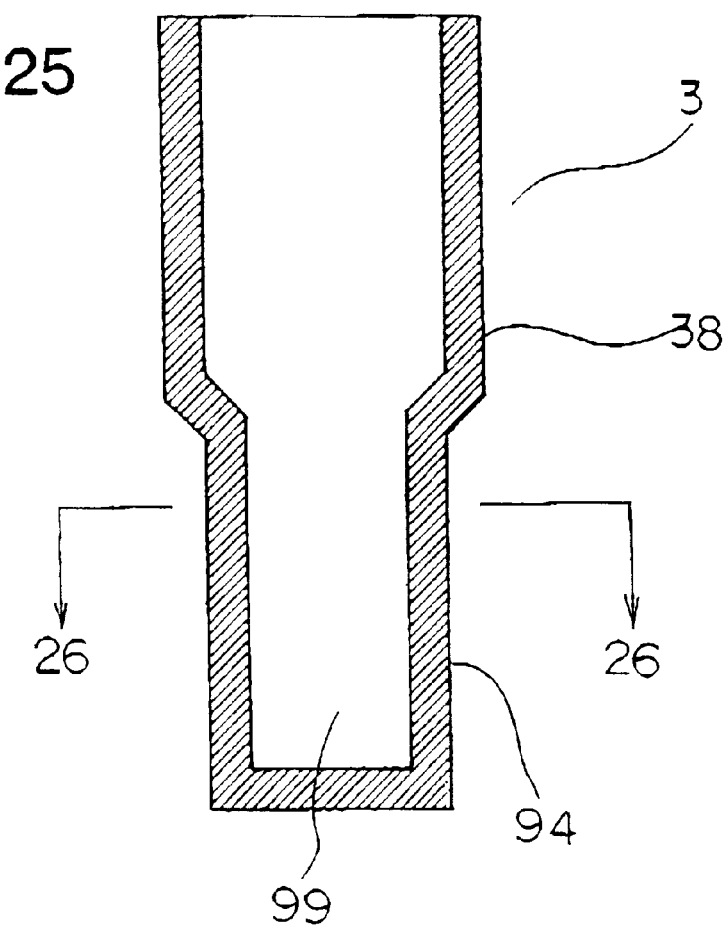
FIG. 25 is a view showing a modified form of the reactive reagent container.
Figure 26:
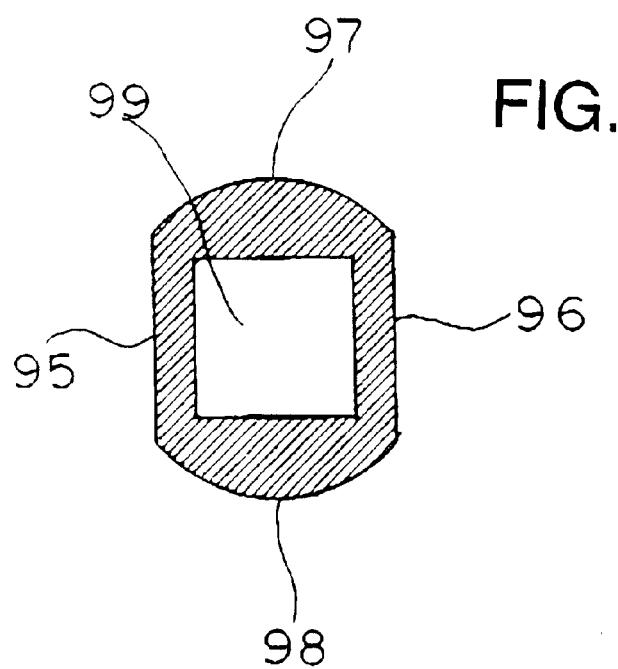
FIG. 26 is a cross-sectional view taken along line 26—26 of 25.

FIGS. 25 and 26 illustrate a separate embodiment of the reactive reagent 3. In this embodiment, a lower part 94 of the measurement container 38 of the reagent container 3 is composed of a thick wall. In addition, the measurement container 38 has at a lower part thereof a square space 99, as shown in FIG. 26, which is defined by side walls 95, 96 with opposite outer peripheries thereof cut off to be flat and with the remaining opposite peripheries kept as they are. With this arrangement, the remaining opposite side walls 97, 98 are rendered capable of functioning as convex lenses. As a result, when light is produced in the measurement container 38, light passed through the side walls 97, 98 is condensed. This is advantageous in that by positioning a luminometer closely to the walls, increased detection sensitivity can be obtained.

Figure 27:
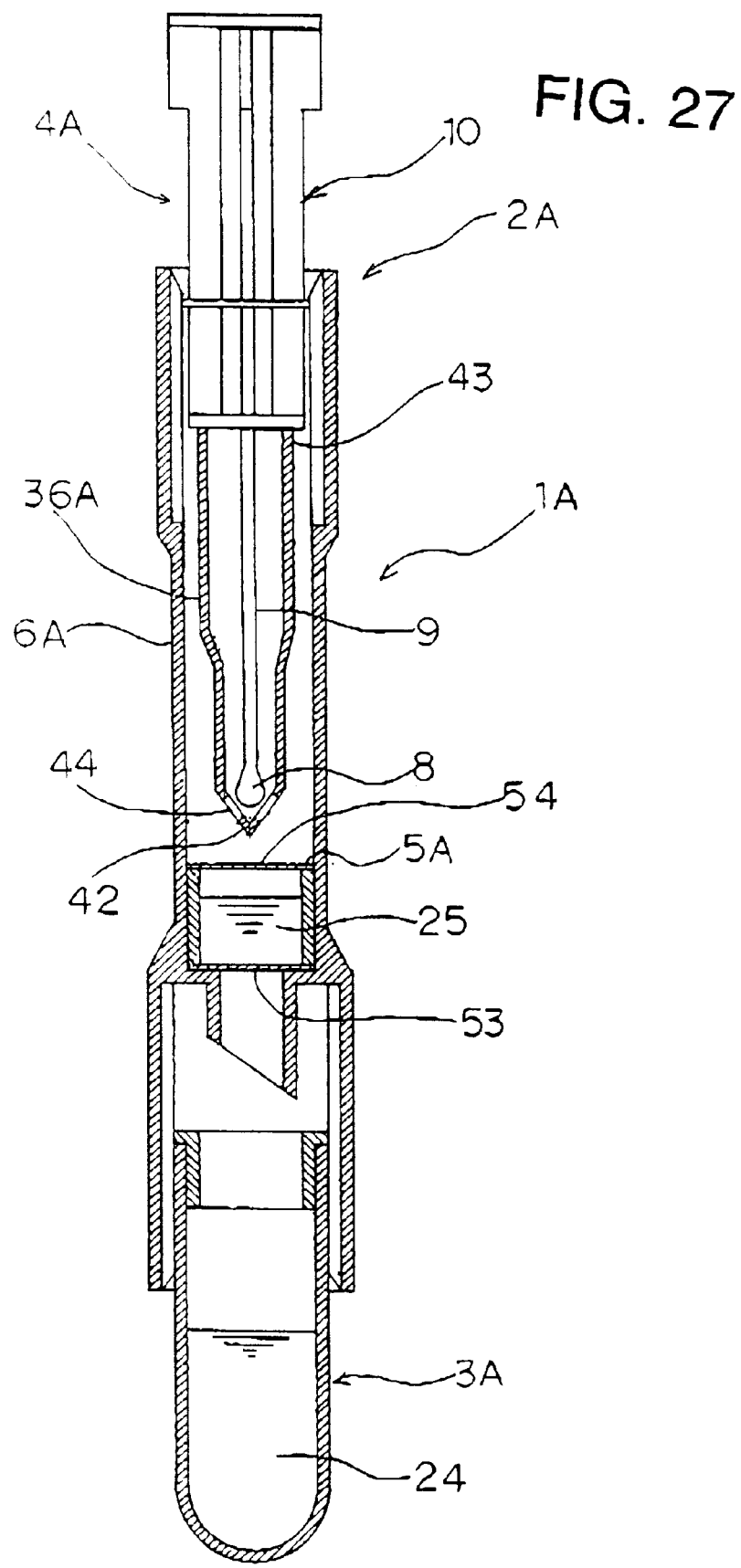
FIG. 27 is a view showing a modified form of the breaker.

FIG. 27 shows a separate embodiment of the breaker. In this embodiment, breaker 36A is formed cylindrically and has an acute-angled or pointed lower end 42. The breaker 36A has an upper end 43 detachably attached to a lower end of the retaining member in such a manner as to enclose the swab 9 in positionally concentric relation thereto. The tip 8 of the swab 9 is positioned closely to the lower acute-angled end 42. The lower end 42 has a circulatory aperture 44 for allowing passage of the extracting liquid 25. Means for attaching the breaker 36A may be, for example, an aperture formed in the lower end of the retaining member 10 for removably receiving the breaker 36A.

In use, the sample wiping member 4A is pulled out of the main body 6A. This is followed by detaching the breaker 36A from the sample wiping member 4A. Next, a sample surface is wiped with the cotton bud 8. Then, the breaker 36 is reloaded onto the sample wiping member 4A and inserted deep into the main body 6A. At this time, the reagent container 3A is pushed upwardly until the seal material 41 is ruptured. Thereafter, the seal material 54 on the upper side of the extracting liquid container 5A is ruptured to cause the swab tip 8 to be contacted with the extracting liquid 25 via the circulatory aperture 44 to thereby transfer the collected bacteria into the liquid 25. Continuously, the sample wiping member 4A is press inserted deeper to rupture the lower seal material 53, thereby causing the liquid 25 to flow down into the reagent container 3A.

Figure 28:
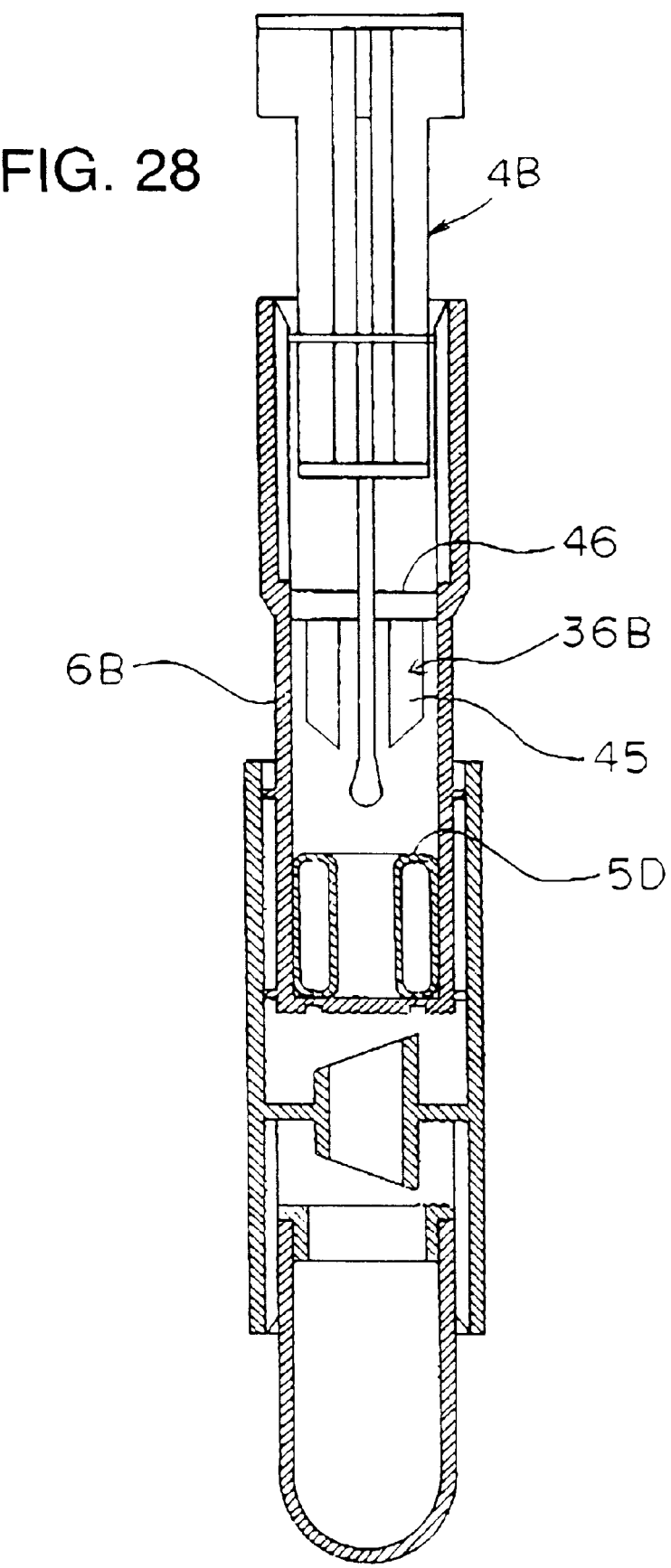
FIG. 28 is a view showing an extraction liquid container and a breaker according to another modification of the present invention.

FIG. 28 illustrates a still further embodiment of the extracting liquid container and the breaker. This embodiment is characterized by the liquid container 5D having an annular shape and the breaker 36B comprised of a cutting member 45 and a retaining member 46 for retaining the cutting member 45.

Extracting liquid container 5D is formed from a material that can be easily ruptured, such as a thin plastic sheet, and is placed on the bottom of the main body 6B. As to the breaker 36B, the retaining member 46 having the cutting member 45 on its underside is disposed at a nearly mid-part of the main body 6B. The retaining member 46 is fitted vertically movably in the cylindrical main body 6B such that it can be fixed at an elected position frictionally. Consequently, in the present embodiment, the breaker 36B keeps staying fitted in the main body 6B and is caused by downward pressing of the sample wiping member 4B to move down to thereby break an extracting liquid container 5D with its cutting member 45.

Figure 29:
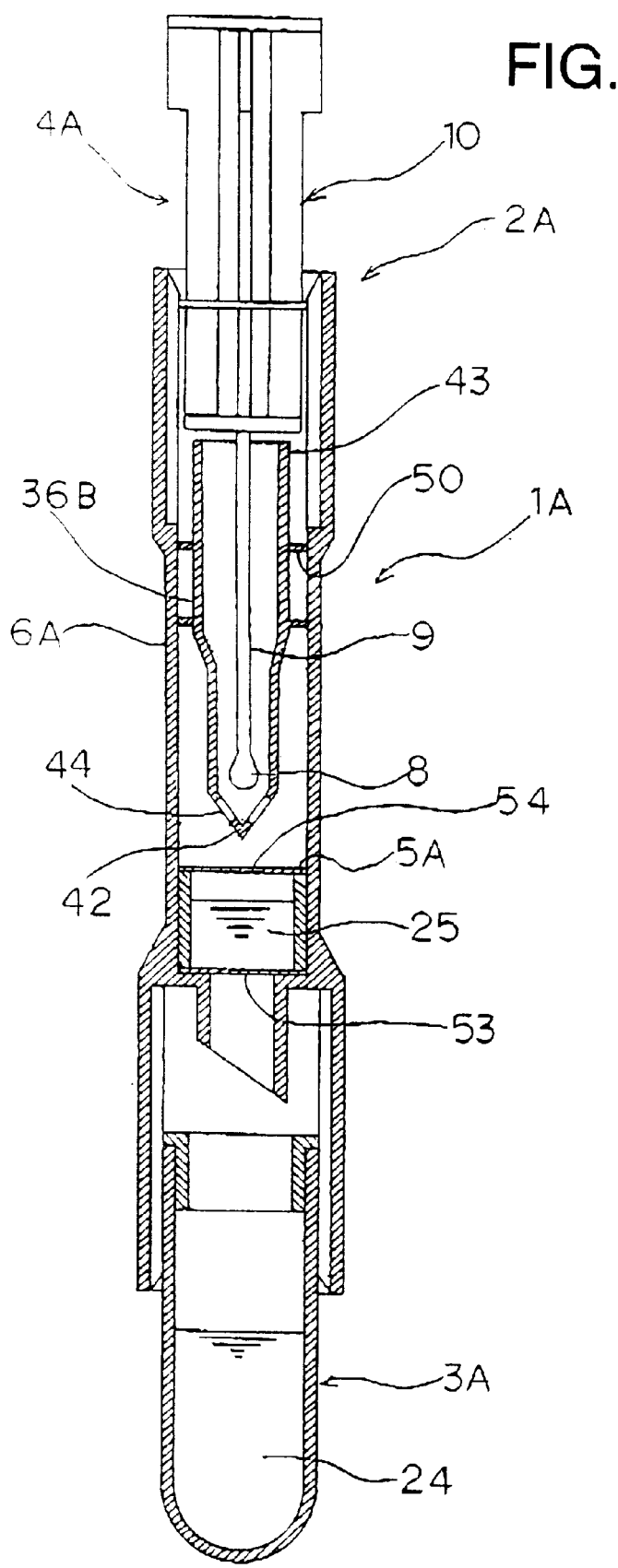
FIG. 29 is a view showing another modification of the breaker.

Reference is now made to FIG. 29 illustrating a further embodiment of the breaker. This embodiment is directed to an alteration of the embodiment of FIG. 27. The breaker 36B is separated from the retaining member 10 and has a brim-shaped member 50. The breaker 36B is vertically movably fitted in the main body 6A. The brim-shaped member 50 has an outer diameter set to allow stoppage of the breaker 36B at an elected position within the main body 6A and to permit vertical movement of the breaker 36B upon pressing of the retaining member 10 from above.

In the embodiment just described, upon removal of the sample wiping member 4A from the main body 6A, the breaker 6B may be left within the main body 6A. Thus, detachment labor as required in the embodiment of FIG. 27 can be omitted. The breaker 36B according to the present embodiment is pressed downwardly by the reinsertion of the sample wiping member 4A, thereby rupturing the seal materials 53, 54.

Figure 30:
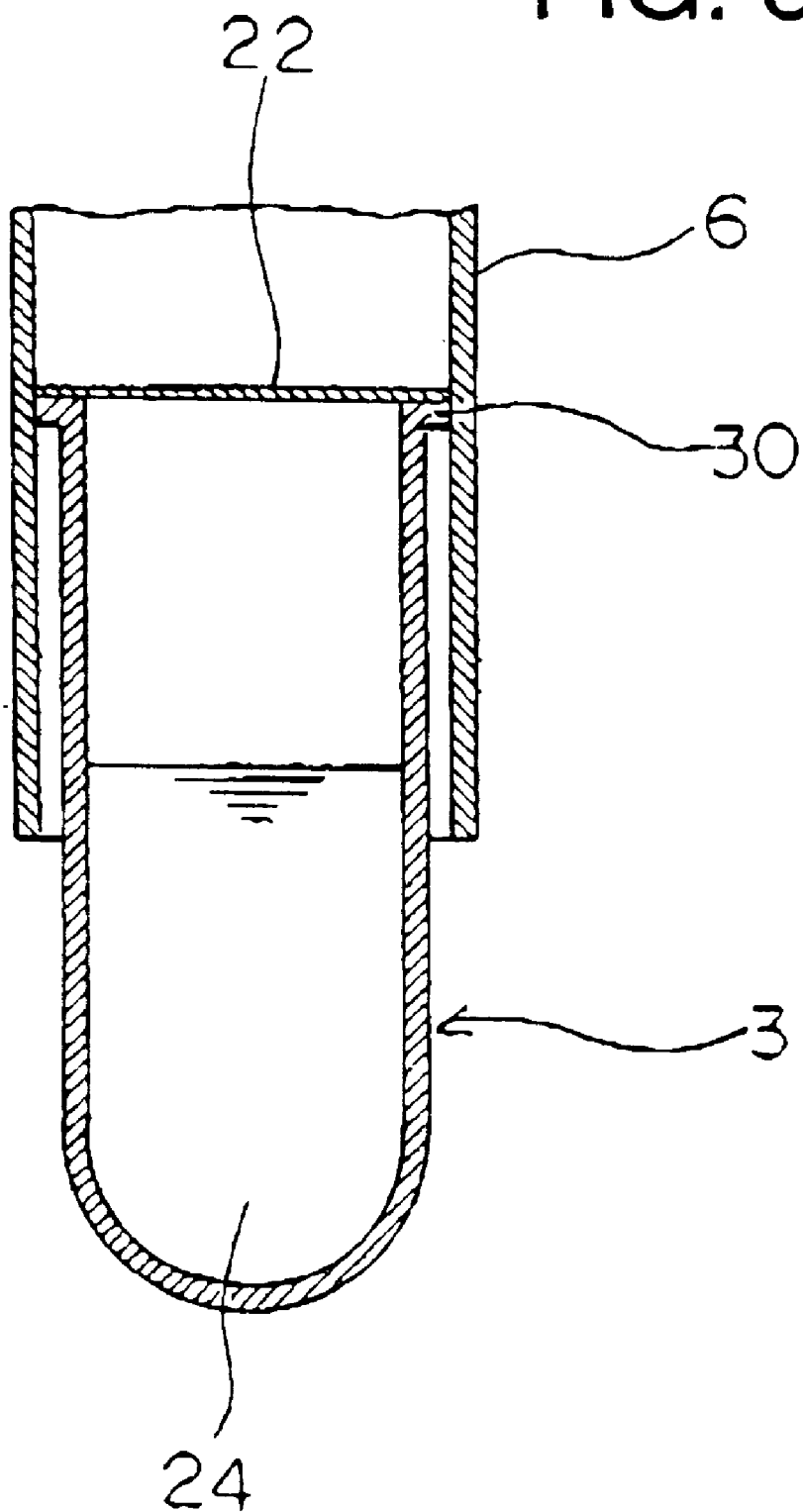
FIG. 30 is a view showing another modification of the reaction reagent container.

FIG. 30 illustrates a separate embodiment of the reagent container 3. This embodiment is directed to an alteration wherein a brim-shaped member 30 is disposed on the upper end of the reactive reagent container 3. With this arrangement, sliding movement of the reagent container 3 relative to the main body 6 becomes smooth and seal effect is achieved between the reagent container and the main body.

Industrial Applicability

By virtue of the present invention thus far explained, sufficient time contact of the swab tip with the extracting liquid is guaranteed and full extraction of the collected bacteria can be achieved, thereby enabling highly precise bacteria measurement. In addition, owing to the splash-proofing member, the extracting liquid can be wholly lead to the reagent container.

What is claimed is:

1. A wipe inspecting instrument comprising:
   a tubular main body having both upper and tower ends thereof opened;

a sample wiping member including a retaining member removably fitted in an upper open part of said main body, and a cotton swab held by said retaining member;

an extracting liquid container disposed within said main body at a position near the open lower end of the main body, said extracting liquid container having upper and lower openings both closed by a first seal material and containing therein an extracting liquid in a sealed fashion, the first seal materials closing the upper and lower openings of the extracting liquid container being designed to be broken in succession by the cotton swab when the sample wiping member is moved downward relative to the main body;

a reactive reagent container having a test tube shape and removably fitted in a lower open part of said main body as to be capable of moving up and down, said reactive reagent container having an upper opening closed by a second seal material and containing therein a reactive reagent in a sealed fashion;

a first breaker disposed within the main body above said reactive reagent container, said second seal material being designed to be broken by the first breaker when the reactive reagent container is moved upward relative to the main body; and a second breaker disposed within the main body above the extracting liquid container, the second breaker having a cantilevered movable piece flexibly deformable to break an upper one of the first seal materials when forced downward by the cotton swab as the sample wiping member is moved downward relative to the main body.

2. A wipe inspection instrument according to claim 1, wherein the movable piece of the second breaker has a sharp-edged projection formed on a lower side of a free end of the movable piece.

3. A wipe inspection instrument according to claim 1, wherein the movable piece of the second breaker has a cutting blade formed on a lower side of a free end of the movable piece.

4. A wipe inspecting instrument according to claim 1, wherein said tubular main body further has a splash-proofing member disposed below the extracting liquid container to prevent the extracting liquid from splashing when the extracting liquid is fed into the reactive reagent container, said splash-proofing member having a lower end forming said breaker.

5. A wipe inspecting instrument according to claim 4, wherein said lower end of the splash-proofing member is beveled at an acute angle.

6. A wipe inspection instrument according to claim 4, wherein said main body and said splash-proofing member has a junction adapted to engage an upper end of said reactive reagent container to stop the reactive reagent container at a given position when the reactive reagent container is moved upward relative to the main body.

7. A wipe inspection instrument according to claim 4, wherein said splash-proofing member has a hollow cylindrical shape.

8. A wipe inspection instrument according to claim 7, wherein said lower end of said hollow cylindrical splash-proofing member is beveled at an acute angle.

9. A wipe inspection instrument according to claim 1, wherein the extracting liquid container further has a plurality of cantilevered lip-off pieces disposed between the first seal materials and located adjacent to a lower one of the first seal materials so as to scrub and squeeze a cotton bud of the cotton when tie cotton bud passes through the ripoff pieces after it pierced past an upper one of the first seal materials.

10. A wipe inspection instrument according to claim 9, wherein the movable piece of the second breaker has a sharp-edged projection formed on a lower side of a free end of the movable piece.

11. A wipe inspection instrument according to claim 10, wherein the movable piece of the second breaker has a cutting blade formed on a lower side of a free end of the movable piece.

12. A wipe inspection instrument according to claim 9, wherein the rip-off pieces have pointed free ends and is flexibly deformable to br the lower first seal material when the cotton bud passes through the rip-off pieces.

13. A wipe inspection instrument according to claim 12, wherein the rip-off pieces have constricted portions at proximal ends thereof.

14. A wipe inspection instrument according to claim 12, wherein the free ends of the rip-off pieces have cutting blades formed on a lower side thereof.

15. A wipe inspection instrument according to, claim 12, wherein the rip-off pieces comprise a plurality of pairs of opposed rip-off pieces, one pair of opposed rip-off pieces of the plurality of pairs of rip-off pieces being longer than the other pair of rip-off pieces.

16. A wipe inspecting instrument comprising:

a tubular main body having both upper and lower ends thereof opened;

a sample wiping member including a retaining member removably fitted in an upper open part of said main body, and a cotton swab held by said retaining member;

an extracting liquid container disposed within said main body at a position near the open lower end of the main body, said extracting liquid container having upper and lower openings both closed by a first seal material and containing therein an extracting liquid in a sealed fashion, the first seal materials closing the upper and lower openings of the extracting liquid container being designed to be broken in succession by the cotton swab when the sample wiping member is moved downward relative to the main body;

a reactive reagent container having a test tube shape and removably fitted in a lower open part of said main body as to be capable of moving up and down, said reactive reagent container having an upper opening closed by a second seal material and containing therein a reactive reagent in a sealed fashion;

a breaker disposed within the main body above said reactive reagent container, said second seal material being designed to be broken by the breaker when the reactive reagent container is moved upward relative to the main body; and a second breaker disposed within the main body above the extracting liquid container for breaking the first seal materials, the second breaker being cylindrically shaped and enclosing the cotton swab, the cylindrically shaped second breaker having an upper end detachably connected to the retaining member and an acute-angled lower end positioned closely to a cotton bud of the cotton swab, the lower end of the second breaker having an aperture for allowing passage of the extracting liquid to cause the cotton bud to be contacted with the extracting liquid when a lower one of the first seal material is ruptured by the second breaker.

17. A wipe inspecting instrument comprising:

a tubular main body having both upper and lower ends thereof opened;

a sample wiping member including a retaining member removably fitted in an upper open part of said main body, and a cotton swab held by said retaining member;

an extracting liquid container disposed within said main body at a position near the open lower end of the main body, said extracting liquid container having upper and lower openings both closed by a first seal material and containing therein an extracting liquid in a sealed fashion, the first seal materials closing the upper and lower openings of the extracting liquid container being designed to be broken in succession by the cotton swab when the sample wiping member is moved downward relative to the main body;

a reactive reagent container having a test tube shape and removably fitted in a lower open part of said main body as to be capable of moving up and down, said reactive reagent container having an upper opening closed by a second seal material and containing therein a reactive reagent in a sealed fashion;

a breaker disposed within the main body above said reactive reagent container, said second seal material being designed to be broken by the breaker when the reactive reagent container is moved upward relative to the main body; and a second breaker disposed above the extracting liquid container for breaking the first seal materials, the second breaker being movably fitted in the main body so that the second breaker is descended as the sample wiping member moves downward relative to the main body, the second breaker being cylindrically shaped and enclosing the cotton swab, the cylindrically shaped second breaker having an acute-angled lower end positioned closely to a cotton bud of the cotton swab, the lower end of the second breaker having an aperture for allowing passage, of the extracting liquid to cause the cotton bud to be contacted with the extracting liquid when a lower one of the first seal material is ruptured by the second breaker.

\* \* \* \* \*